United States Patent
SaNogueira et al.

(10) Patent No.: US 11,590,067 B2
(45) Date of Patent: Feb. 28, 2023

(54) HYDROPHOBIC TOPICAL COMPOSITIONS AND METHODS FOR PRODUCING SAME

(71) Applicant: Edgewell Personal Care Brands, LLC, Chesterfield, MO (US)

(72) Inventors: James SaNogueira, Wesley Hills, NY (US); Tao Zheng, New City, NY (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 0 days.

(21) Appl. No.: 15/412,018

(22) Filed: Jan. 22, 2017

(65) Prior Publication Data

US 2018/0000721 A1  Jan. 4, 2018

Related U.S. Application Data

(60) Provisional application No. 62/281,854, filed on Jan. 22, 2016.

(51) Int. Cl.

| | | |
|---|---|---|
| *A61K 8/02* | (2006.01) | |
| *A61K 8/891* | (2006.01) | |
| *A61K 8/25* | (2006.01) | |
| *A61K 8/29* | (2006.01) | |
| *A61K 8/34* | (2006.01) | |
| *A61K 8/37* | (2006.01) | |
| *A61Q 17/02* | (2006.01) | |
| *A61Q 17/04* | (2006.01) | |
| *A61K 8/27* | (2006.01) | |
| *A61K 8/87* | (2006.01) | |
| *A61K 8/73* | (2006.01) | |
| *A61K 8/81* | (2006.01) | |
| *A61K 8/89* | (2006.01) | |
| *A61K 8/35* | (2006.01) | |
| *A61K 8/893* | (2006.01) | |
| *A61Q 17/00* | (2006.01) | |

(52) U.S. Cl.
CPC .............. *A61K 8/891* (2013.01); *A61K 8/25* (2013.01); *A61K 8/27* (2013.01); *A61K 8/29* (2013.01); *A61K 8/34* (2013.01); *A61K 8/35* (2013.01); *A61K 8/37* (2013.01); *A61K 8/731* (2013.01); *A61K 8/8111* (2013.01); *A61K 8/8147* (2013.01); *A61K 8/8152* (2013.01); *A61K 8/87* (2013.01); *A61K 8/89* (2013.01); *A61K 8/893* (2013.01); *A61Q 17/00* (2013.01); *A61Q 17/02* (2013.01); *A61Q 17/04* (2013.01); *A61K 2800/31* (2013.01); *A61K 2800/43* (2013.01); *A61K 2800/54* (2013.01)

(58) Field of Classification Search
CPC ........ A61K 8/0241; A61K 8/04; A61K 8/042; A61K 8/044; A61K 8/06; A61K 8/14; A61K 8/19; A61K 8/25; A61K 8/27; A61K 8/31; A61K 8/731; A61K 8/72; A61K 8/73; A61K 8/732; A61K 8/735

See application file for complete search history.

(56) References Cited

U.S. PATENT DOCUMENTS

| | | | |
|---|---|---|---|
| 3,574,791 A | 4/1971 | Sherman et al. | |
| 4,795,631 A | 1/1989 | Sheehan | |
| 5,069,897 A * | 12/1991 | Orr | A61K 8/25 424/66 |
| 5,500,216 A | 3/1996 | Julian et al. | |
| 5,540,853 A * | 7/1996 | Trinh | A61K 8/02 510/101 |
| 5,925,337 A | 7/1999 | Arraudeau et al. | |
| 5,985,297 A | 11/1999 | Mellul et al. | |
| 6,335,037 B1 | 1/2002 | Ichinohe et al. | |
| 6,967,024 B2 * | 11/2005 | Scancarella | A61Q 1/02 424/70.7 |
| 7,037,515 B2 | 5/2006 | Kalafsky et al. | |
| 8,513,342 B2 | 8/2013 | Gao et al. | |
| 8,999,307 B2 | 4/2015 | Ranade et al. | |
| 9,005,591 B2 | 4/2015 | Ranade et al. | |
| 9,115,424 B2 | 8/2015 | Aria et al. | |
| 9,585,831 B2 | 3/2017 | Ao et al. | |
| 2002/0018791 A1 * | 2/2002 | Vatter | A61K 8/891 424/401 |
| 2003/0113357 A1 * | 6/2003 | Bell | A61K 8/345 424/401 |
| 2009/0214628 A1 * | 8/2009 | de Rijk | A01N 59/00 424/47 |
| 2010/0266648 A1 | 10/2010 | Ranade et al. | |
| 2011/0008401 A1 * | 1/2011 | Ranade | A61K 8/585 424/125 |
| 2012/0040577 A1 | 2/2012 | Kissel et al. | |

(Continued)

FOREIGN PATENT DOCUMENTS

| | | |
|---|---|---|
| CN | 1430500 A | 7/2003 |
| CN | 101903005 A | 12/2010 |
| CN | 101980686 A | 2/2011 |

(Continued)

OTHER PUBLICATIONS

Rust-Oleum Material Safety Data Sheet, Jul. 5, 2013.
International Search Report and Written Opinion issued in connection with PCT Application No. PCT/US2017/014475 dated Mar. 10, 2017.
Anonymous "Suncare Compositions with New Cosmetic Raw Materials (6)", IP.Com Journal, West Henrietta, NY US, Dec. 15, 2015, 115 pages.
EP Examination issued in connection with EP Application No. 17702287.8 dated Oct. 23, 2019.
International Preliminary Report on Patentability issued in connection with PCT Application No. PCT/US2017/014475 dated Jul. 24, 2018.

(Continued)

*Primary Examiner* — Micah Paul Young (57) ABSTRACT

An anhydrous topical composition provides a water repellent surface. The anhydrous topical composition has at least one film former with surface tension lower than 35 dynes/cm, at least one particle having a hydrophobic surface or a hydrophobic surface treatment, and a volatile topical carrier.

22 Claims, 4 Drawing Sheets

(56) References Cited

U.S. PATENT DOCUMENTS

| | | | |
|---|---|---|---|
| 2012/0058330 A1 | 3/2012 | Smith et al. | |
| 2014/0107228 A1* | 4/2014 | Togashi | A61K 8/73 |
| | | | 514/777 |

FOREIGN PATENT DOCUMENTS

| | | |
|---|---|---|
| CN | 102525840 A | 7/2012 |
| CN | 104411284 A | 3/2015 |
| CN | 105246454 A | 1/2016 |
| WO | 0018367 A1 | 4/2000 |
| WO | 2009082565 A1 | 7/2009 |
| WO | 2009111128 A1 | 9/2009 |
| WO | 2012064482 A1 | 5/2012 |
| WO | 2014101698 A1 | 7/2014 |

OTHER PUBLICATIONS

Shang et al., "Nanostructured Superhydrophobic Surfaces", Journal of Materials Science, vol. 40, 2005, pp. 3587-3591, XP019210466.

Lau et al., "Superhydrophobic Carbon Nanotube Forests", Nano Letters, 2003, vol. 3, No. 12, pp. 1701-1705.

Ren et al., "Preparation and Characterization of an Ultrahydrophobic Surface Based on a Stearic Acid Self-Assembled Monolayer over Polyethyleneimine Thin Films", Surface Science, 2003, vol. 546, pp. 64-74 XP055205049.

Unofficial translation of Chinese Office Action and Search Report issued in connection with CN Application No. 201780020353.X dated Dec. 24, 2020.

Unofficial translation of Chinese Office Action and Search Report issued in connection with CN Application No. 201780020353.X dated Sep. 22, 2021.

* cited by examiner

| Product Name | Initial Contact Angle | Contact Angle after 1 minute |
|---|---|---|
| BANANA BOAT Sport Lotion SPF30 | | 11.3° 11.3° |
| NEUTROGENA Beach Defense Lotion SPF30 | | 5.5° 5.5° |
| COPPERTONE Sport Lotion SPF30 (2016) | 61.0° 61.0° | 20.3° 20.3° |
| Example 9 | 138.2° 138.2° | 133.3° 133.3° |
| Example 18 | 155.0° 155.0° | 155.0° 155.0° |

HYDROPHOBIC TOPICAL COMPOSITIONS AND METHODS FOR PRODUCING SAME

CROSS REFERENCE TO RELATED APPLICATIONS

This application claims priority to U.S. Provisional Application Ser. No. 62/281854, filed on Jan. 22, 2016, the contents of which are incorporated herein for reference in its entirety.

BACKGROUND OF THE INVENTION

Field of the Invention

The invention involves chemical compositions capable of repelling water. Specifically, the invention involves chemical compositions, safe for application to human skin, capable of repelling water by imparting hydrophobic of superhydrophobic characteristics into topical formulae.

Description of Related Art

Water repellency or durability is one of key performance characteristics in certain topical compositions including long-wearing color cosmetics and water resistant sunscreens. Conventional technologies in cosmetics and sunscreens have focused on staying power on skin, such as long-lasting skin adhesion or water resistance of cosmetic actives. Many film formers have been used to enhance the durability of cosmetic and other topical compositions on human skin. Typically, when a topical composition is exposed to water, such as through sweating or swimming, the water starts to wet the composition surface. A wet surface ultimately results in a lack of durability in a topical composition. This lack of durability is caused by a loss of topical actives due to any re-emulsification process.

Past compositions attempted to create water resistant surfaces, whereas hydrophobic or superhydrophobic technology creates a water repellent surface. A water repellent surface creates a physical interaction with water molecules, so that water will bead up and roll off the topical surface without wetting the surface. Water repellency not only provides a desirable dry feel on skin but also creates a visual cue for formula durability on skin.

Hydrophobicity is measured by the water contact angle. The water contact angle on a surface is the angle of the leading edge of a water droplet on the surface as measured from the center of the interface between the droplet and the surface. A surface with a contact angle of 180 degrees means that water sits on the surface as a perfect sphere. Hydrophobic surfaces, when measured, have a contact angle between 90 degrees and 150 degrees. Superhydrophobic surfaces, when measured, have a contact angle between 150 degrees and 180 degrees.

A superhydrophobic surface can cause water to roll off the surface leaving little or no residue. Hydrophobic surfaces are desirable in many arts for varied uses and are created through varying means. For example, a superhydrophobic surface can be created on polytetrafluoroethylene (PTFE) with a picosecond laser for use on underwater materials (Shang et al., "Nanostructured Superhydrophobic Surfaces," 40 J. MATER . Sci. . 3587 (2005)). Carbon nanotubules also can achieve a superhydrophobic surface through deoxygenation of a chemical treatment (Lau et al., "Superhydrophobic Carbon Nanotube Forests," 3 NANO LETTERS 1701 (2003); U.S. Pat. No. 9,115,424). Additionally, acid absorbed onto aluminum coated in polyethyleneimine (PEI) can create a superhydrophobic surface (Ren et al., "Preparation and Characterization of an Ultrahydrophobic Surface Based on a Stearic Acid Self-Assembled Monolayer over Polyethyleneimine Thin Films," 546 SURFACE SCIENCE 64 (2003)).

Film formers are known to be used in topical compositions to create water resistant barriers. Film formers are durable water resistant polymers that have wide use in industrial processes. When applied to a surface, film formers act as a barrier between the surface and any outside matter, such as water. Film formers are commercially available in many different forms. Emulsion-based film formers are typically water-in-oil or water-in-silicone emulsions. The use of such emulsions relies on the water evaporating and leaving the oil or the silicone in contact with the skin to produce a water resistant layer. However, the use of emulsion-based film formers creates unpleasant aesthetics on the skin, such as an oily appearance and a greasy feel. The resulting film is not water repellent and leaves an unnatural appearance on the skin.

Anhydrous film formers typically include organic solvents, such as an alcohol. Such film formers can also produce a tacky feeling on human skin and other undesirable aesthetics when introduced to water. Representative patents regarding such water resistant topical compositions are set forth below in Table 1.

TABLE 1

| 1 | U.S. Pat. No. 5,985,297 | Anhydrous and water-resistant cosmetic compositions |
|---|---|---|
| 2 | U.S. Pat. No. 5,925,337 | Waterproof compositions for covering the eyelashes, and process for the preparation thereof |
| 3 | U.S. Pat. No. 4,795,631 | Water based lip color comprising an alkali soluble film-forming agent |

Film formers conventionally used in topical compositions alone do not reach a desirable level of hydrophobicity that imparts durability. Ideally, a topical composition has a superhydrophobic surface that creates a water contact angle of 150 degrees or more. Table 2 below shows that most film formers alone can barely achieve a water contact angle greater than 100 degrees, while it is desirable to achieve a surface hydrophobicity where the contact angle of water is 130 degrees or greater. It should also be noted that upon incorporation into a topical composition with various other ingredients, such contact angles are difficult to maintain.

TABLE 2

| Polymer Name | CAS No. | $\gamma S$ Critical Surface Tension (dynes/cm) | Contact Angle with Water (°) |
|---|---|---|---|
| Polyvinyl alcohol (PVOH) | 25213-24-5 | 37 | 51 |
| Nylon 6 (polycaprolactum, aramid 6) | 25038-54-4 | 43.9 | 62.6 |
| Polyethylene oxide (PEO, PEG) | 25322-68-3 | 43 | 63 |
| Polymethylmethacrylate (PMMA, acrylic) | 9011-14-7 | 37.5 | 70.9 |
| Polystyrene (PS) | 9003-53-6 | 34 | 87.4 |
| Polybutadiene | 9003-17-2 | 29.3 | 96 |
| Polyethylene (PE) | 9002-88-4 | 31.6 | 96 |
| Polydimethylsiloxane (PDMS) | 9016-00-6 | 20.1 | 107.2 |
| Paraffin (Wax) | 8002-74-2 | 24.8 | 108.9 |
| Polytetrafluoroethylene (PTFE) | 9002-84-0 | 19.4 | 109.2 |
| Polyisobutylene (PIB, butyl rubber) | 9003-27-4 | 27 | 112.1 |

Despite the many advances in water resistant topical compositions, there is still a need for a water repellent topical composition that provides pleasant and desirable aesthetics for consumers.

SUMMARY OF THE INVENTION

In a first aspect, the present invention is directed to an anhydrous topical composition comprising at least one film former having a surface tension lower than 35 dynes/cm selected from the group consisting of glycol ester crosspolymers, silicones, resins and derivatives thereof, and olefinic polymers and crosspolymers, said at least one film former is present in an amount of 5% to 10% by weight based on a total weight of said anhydrous topical composition; particles comprising hydrophobic-treated silica, fumed silica, polytetrafluoroethylene, polyurethane, silica silylate, polymethylsilsesquioxane, hydrophobic-treated calcium silicate, hydrophobic-treated cellulose, hydrophobic-treated polymethylmethacrylate, hydrophobic-treated zinc oxide, hydrophobic-treated titanium dioxide, or combinations thereof, said particles present in an amount of 1.5% to 10% by weight based on the total weight of said anhydrous topical composition; a volatile topical carrier present in an amount of 30% to 60% by weight based on the total weight of said anhydrous topical composition; and an active agent selected from the group consisting of a sunscreen active agent, an insect repellent, a colorant, and combinations thereof; wherein said anhydrous topical composition has an initial water contact angle greater than 90 degrees.

The active agent may comprise a therapeutic amount of at least one sunscreen active agent selected from the group consisting of an ultraviolet A long-wave sunscreen active agent, an ultraviolet B shortwave sunscreen active agent, a full spectrum sunscreen active agent, an encapsulated UV filter, and combinations thereof. The active agent may also comprise a therapeutic amount of at least one insect repellent selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, natural essential oils, p-menthane-3,8-diol, and mixtures thereof. Alternatively, the active agent comprises at least one colorant selected from the group consisting of an organic pigment or dye, an inorganic pigment or dye, and mixtures thereof.

Preferably, the anhydrous topical composition has an initial water contact angle greater than 120 degrees. More preferably, the anhydrous topical composition has a water contact angle greater than 60 degrees after 40 minutes.

In another aspect, the present invention is also directed to an anhydrous sunscreen composition comprising a sunscreen active agent comprising avobenzone, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimate, titanium dioxide, zinc oxide, bis-octrizole, bemotrizinol, drometrizole trisiloxane, sulisobenzone, dioxybenzone, encapsulated UV filters, or combinations thereof; at least one film former having a surface tension lower than 35 dynes/cm wherein the film former is selected from the group consisting of a polymer, a wax, an ester, a resin, a rosin, a silicone, a silicone resin, and a fluorinated silicone; particles comprising hydrophobic-treated silica, fumed silica, polytetrafluoroethylene, polyurethane, silica silylate, polymethylsilsesquioxane, hydrophobic-treated calcium silicate, hydrophobic-treated cellulose, hydrophobic-treated polymethylmethacrylate, hydrophobic-treated zinc oxide, hydrophobic-treated titanium dioxide, or combinations thereof; and a volatile topical carrier; wherein said anhydrous sunscreen composition has an initial water contact angle greater than 90 degrees and a water contact angle of at least 60 degrees after 40 minutes. Preferably, the anhydrous sunscreen composition has an initial water contact angle greater than 100 degrees and a water contact angle of at least 60 degrees after 80 minutes.

In yet another aspect, the present invention is directed to an anhydrous topical composition comprising at least one film former having a surface tension lower than 35 dynes/cm; hydrophobic particles comprising hydrophobic-treated silica, fumed silica, polytetrafluoroethylene, polyurethane, silica silylate, polymethylsilsesquioxane, hydrophobic-treated calcium silicate, hydrophobic-treated cellulose, hydrophobic-treated polymethylmethacrylate, hydrophobic-treated zinc oxide, hydrophobic-treated titanium dioxide, or combinations thereof; and a volatile topical carrier; wherein said composition has an initial water contact angle greater than 90 degrees.

Preferably, the anhydrous topical composition further includes an active agent comprising sunscreen active agents; insect repellents; colorants; amino acids; moisturizers; pH adjusters; perfumes; essential oils; essential fatty acids; sphingolipids; antioxidants; chelating agents; emollients; humectants; moisturizers; minerals; keratolytics; retinoids; hormones; alpha-keto acids; anti-mycobacterial agents; antifungal agents; anti-microbials; anti-virals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; skin cooling compounds; skin warming compounds; skin protectants; skin penetration enhancers; exfoliants; lubricants; depigmenting agents; hypopigmenting agents; pharmaceutical agents; photostabilizing agents; plant extracts; absorbents; salicylic acid; alpha and beta hydroxy acids; vitamins including vitamins A, C, and E; retinol and its derivatives; or combinations thereof.

Most preferably, the active agent comprises a sunscreen active agent selected from the group consisting of avobenzone, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimate, titanium dioxide, zinc oxide, bis-octrizole, bemotrizinol, drometrizole trisiloxane, sulisobenzone, dioxybenzone, encapsulated UV filters, and combinations thereof. Alternatively, the active agent comprises at least one insect repellent being a member selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, natural essential oils, p-menthane-3,8-diol, and mixtures thereof.

Preferably, the anhydrous topical composition has an initial water contact angle greater than 100 degrees, and more preferably, an initial water contact angle greater than 150 degrees. More preferably, the anhydrous topical composition has a water contact angle greater than 60 degrees after 40 minutes, and most preferably, a water contact angle greater than 60 degrees after 80 minutes.

Preferably, the at least one film former is present in an amount of 0.5% to 20% by weight based on a total weight of said composition and is selected from the group consisting of glycol ester crosspolymers, silicones, resins and derivatives thereof, and olefinic polymers and crosspolymers. Preferably, the particles are present in an amount of 0.5% to 15% by weight based on a total weight of said composition. Preferably, the volatile topical carrier is present in an amount of 10% to 80% by weight based on a total weight of said composition and is selected from the group consisting of a volatile hydrocarbon, a volatile silicone fluid, ethanol, and combinations thereof.

The inventive compositions may be one of a lotion, a cream, an emulsion, a gel, a suspension, an aerosol, or a powder.

DETAILED DESCRIPTION OF THE INVENTION

The embodiments of the present disclosure can comprise, consist of, and consist essentially of the features and/or steps described herein, as well as any of the additional or optional ingredients, components, steps, or limitations described herein or would otherwise be appreciated by one of skill in the art. It is to be understood that all concentrations disclosed herein are by weight percent based on a total weight of the composition unless otherwise indicated. Any numerical range recited herein is intended to include all sub-ranges subsumed therein, and such ranges are understood to include each and every number and/or fraction between the stated range lower and upper values. For example, a range of about 0.5% and 15% by weight of hydrophobic particles would expressly include all intermediate values of 0.6, 0.7, 0.8, all the way up to and including 14.7, 14.7, 14.9 and 15% by weight of hydrophobic particles. The same applies to all other composition ranges set forth herein. Where appropriate, the INCI (International Nomenclature of Cosmetic Ingredients) name of ingredients/components is provided.

Given the broad applicability of the teachings of the present specification, it is not possible to discuss each and every use and application of the present invention and certainly not in any detail. Rather, the following specification, while mentioning a number of specific teachings, is primarily focused on general topical compositions, such as sunscreens, make-up, and insect repellents, though these teachings are applicable to any number of cosmetic, skin care, health and beauty aid products including, but not limited to, personal cleansing products such as soaps, shampoos, gels, fragrances, as well as food, household cleaning, sanitizing, odor control products, etc.

The present invention provides an anhydrous topical composition having at least one film former with surface tension lower than 35 dynes/cm, at least one particle having a hydrophobic surface or hydrophobic surface treatment, and a volatile topical carrier. Unexpectedly, the anhydrous topical composition has an initial water contact angle greater than 60 degrees, preferably greater than 90 degrees, and most preferably greater than 100 degrees, and wherein the contact angle of the composition can be maintained for an extended period of time greater than forty (40) minutes or longer, preferably for eighty (80) minutes or longer. Embodiments of the invention include one or more active agents that are added to the anhydrous topical composition to provide a desirable dermatological effect. Desirable active agents may include a sunscreen active agent, an insect repellent active agent, a colorant, a fragrance or combinations of these active agents. These and other embodiments of the anhydrous topical composition can be produced either in spray form, anhydrous lotion form, or other forms known in the pharmaceutical, cosmetic, and similar arts. Anhydrous is considered to be less than 1% by weight water based on a total weight of the composition.

It has been found that using a layer of hydrophobic particles along with a film former with a surface tension lower than 35 dynes/cm produces a water repellent surface in a topical composition. The hydrophobic particles increase the surface roughness of any applied layer and are added to the topical composition to create a micro-roughness on the skin. The advantage of adding particles is that the micro-roughness increases the hydrophobicity of the topical composition by creating hydrophobic peaks to support and repel water droplets while still producing an overall desirable smoothness to the surface of the topical composition. However, pockets are formed in the particle layer where water can move freely through. A film former with a surface tension lower than 35 dynes/cm used in connection with a hydrophobic particle layer covers these pockets in the particle layer, and together the film former and particle layer create a water repellent surface when formulated into a topical composition.

Film formers useful in the inventive compositions must have a surface tension lower than 35 dynes/cm. Such preferred film formers can be, but are not limited to, glycol ester crosspolymers, silicones, resins and derivatives thereof, and olefinic polymers and crosspolymers, and combinations thereof. Glycol esters having a surface tension Sower than 35 dynes/cm may include, without limitation, adipic acid/diglycol crosspolymer (LEXOREZ® 100), trimethylpentanediol/adipic acid/glycerin crosspolymer (LEXOREZ 200), polyester-7 (and) neopentyl glycol diheptanoate (LEXFILM® Sun), polyester-10 (and) propylene glycol dibenzoate (LEXFILM Spray), and combinations thereof. Preferred silicones having a surface area lower than 35 dynes/cm may include, without limitation, ethanol (and) crotonic acid/vinyl $C_{8-12}$ isoalkyl esters/vinyl acetate/bis-vinyldimethicone crosspolymer (BELSIL® P1101), acrylates/dimethicone copolymer (KP-550), trimethylsiloxysilicate (MQ resin), $C_{24-28}$ alkyldimethylsiloxy trimethylsiloxysilicate (GRANRESIN MQI-2450, GRANRESIN MQC-2450), polymethylsilsesquioxane/trimethylsiloxysilicate (GRANRESIN MQI-T50, GRANRESIN MQC-T50), polymethylsilsesquioxane (GRANRESIN PMSQ-ID, GRANRESIN PMSQ-FLUID, GRANRESIN PMSQ-$C_9$), perfluorononyl dimethicone (PECOSIL® FSH-1500), perfluorononyl dimethicone (PECOSIL FSH-300), Trifluoropropyldimethylsiloxy/Trimethylsiloxy Silsesquioxane (and) Dimethicone (SILFORM® FR-5), Trifluoropropyldimethylsiloxy/Trimethylsiloxy Silsesquioxane (and) Dimethicone (SILFORM FR-10) or any combinations thereof. Resins may include, without limitations, its rosin derivatives, and abietic acid derivatives such as methyl dihydroabietate (MERISTANT® 101L). Olefinic polymers useful as film formers having a surface tension lower than 35 dynes/cm may include hydrogenated polycyclopentadiene (and) isododecane (KOBOGUARD® 5400 IDD).

A film former with a surface tension lower than 35 dynes/cm typically comprises between 0.5% and 20% by weight of the composition. A preferred range of the film former is between 5% and 10% by weight of the composition.

Particles useful in the present invention can be a hydrophobic-treated silica or fumed silica, a polytetrafluoroethylene, a polyurethane, a silica silylate, a polymethylsilsesquioxane, a hydrophobic-treated calcium silicate, a hydrophobic-treated cellulose, a hydrophobic-treated PMMA, a hydrophobic-treated zinc oxide, a hydrophobic-treated titanium dioxide, and combinations thereof. Such surface treated particles are sold under the trade names EA-209, FLO-BEADS® SE-3107A, BPD-800, BPD-500, BPD-500T, BPA-500, MSP-822, BPA-500X, MSP-930, MSP-825, TR-1, TR-2, POMP900, SP-10, SP-500, DAIAMID® MSP-100, DAIAMID MSP-BIO, DAIAMID MSP-S, CL-2080, ECOBEADS® D-1, ECOBEADS D-5, DIASPHERE® KS-500, DIASPHERE KS-1000, MST-203, MST-547, TOSPEARL® 145A, TOSPEARL 2000B, TOSPEARL 3000A, TOSPEARL 150KA, TOSPEARL 1110A, TOSPEARL 120A, SESQ-ML5, SESQ-MH5, SESQ-White1, SESQ-CL3, SESQ-CH1, MSS-500, MSS-500W, MSS-500/N, MSS-500/7N, MSS-500/H, MSS-500/3, MSS-500/3N, MSS-500/3H, MSS-500/3H4, MSS-500/20N, SILICA SHELLS, FLORITE® R, FLORITE PS-10, CELLULOBEADS D-5, CELLULOBEADS D-10, CELLULOBEAOS D-30, CELLULOBEADS D-50, CELLULOBEADS USF, CELLULOBEADS D-10(R-33P), CELLULOBEADS D-10(Y-33P), CELLULOBEADS D-10(UB-33), CELLULOBEADS D-10(Ti-33), CAB-O-SIL® TS-530, CAB-O-SIL TS-610, CAB-O-SIL TS-710, CAB-O-SIL TS-720, AEROSIL® R 972, AEROSIL R974, AEROSIL R 104, AEROSIL R 106, AEROSIL R 202, AEROSIL R 208, AEROSIL R 805, AEROSIL R 812, AEROSIL R 812 S, AEROSIL R 816, AEROSIL R 7200, AEROSIL R 8200, AEROSIL R 9200, AEROSIL R 711, AEROSIL RY 50, AEROSIL NY 50, AEROSIL NY 50 L, AEROSIL RY 200, AEROSIL RY 200 S, AEROSIL RX 50, AEROSIL NAX 50, AEROSIL® RX 200, AEROSIL RX 300, AEROSIL R 504, AEROSIL NX 90 S, AEROSIL NX 90 G, AEROSIL RY 300, AEROSIL REA 90, AEROSIL REA 200, AEROSIL RY 51, AEROSIL NA 50 Y, AEROSIL RA 200 HS, AEROSIL NA 50 H, AEROSIL RA 200 H, AEROSIL NA 130 K, AEROSIL NA 200 Y, AEROSIL NX 130, AEROSIL RY 200 L, R 709, AEROSIL R 976 S, AEROSIL R 972 Pharma, HDK® H13L, HDK H15, HDK H17, HDK H18, HDK H20, HDK H2000, HDK N20, HDK N20 NUTRITION, HDK N20 PHARMA, HDK N20P, HDK N20P, HDK N20ST, HDK S13, HDK T30, HDK T30P, HDK T40, HDK T40 NUTRITION, HDK V15, HDK V15A, HDK V15D, and combinations thereof.

The particles may have a particle size of about 0.1 to about 50 microns; preferably, a particle size of about 0.1 to about 30 microns, and most preferably a particle size of about 0.2 to about 20 microns.

The particles typically comprise between 0.5% and 15% by weight of the composition. A preferred range of the particles is between 1.5% and 10% by weight of the composition.

The volatile topical carrier useful in the present invention can be either polar or non-polar and can be, but is not limited to, ethanol, isododecane, volatile hydrocarbons such as isobutane, or volatile silicones such as cyclopentasiloxane disilaxane, and combinations thereof.

For the non-polar, volatile topical carriers, a non-polar, volatile oil tends to impart highly desirable aesthetic properties to the compositions of the present invention. Consequently, the non-polar, volatile oils are preferably utilized at a fairly high level of commercial products. Non-polar, volatile oils particularly useful in the present invention include a member selected from the group consisting of silicone oils, hydrocarbons, and mixtures thereof. The non-polar, volatile oils useful in the present invention can be either saturated or unsaturated, have an aliphatic character and be straight or branched chained or contain alicyclic or aromatic rings. Examples of preferred non-polar, volatile hydrocarbons include $C_{10}$-$C_{12}$ alkanes, such as isododecane (e.g., PERMETHYL®-99A which is available from Presperse Inc.), isodecane, and the $C_7$-$C_8$ through $C_{12}$-$C_{15}$ isoparaffins (such as the ISOPAR® Series available from Exxon Chemicals Corp.), Highly preferred examples of proprietary commercial volatile silicone fluids include cyclomethicones of varying viscosities, e.g., Dow Corning 200, Dow Corning 244, Dow Corning 245, Dow Corning 344, and Dow Corning 345, (commercially available from Dow Corning Corporation); SF-1204 and SF-1202 Silicone Fluids (commercially available from G.E. Silicones); GE 7207 and 7158 (commercially available from General Electric Co.); and SWS-03314 (commercially available from SWS Silicones Corp.). Additionally, linear silicones can be used, including, but not limited to, dimethicones having a viscosity of about 0.65 centistokes to about 2.0 centistokes For the polar, volatile topical carriers, two different categories are desirable. The first category is the use of ethanol alone. The second category is a mixture of ethanol with isododecane or linear dimethicones.

The volatile topical carrier typically comprises between 10% to 80% by weight of the composition. A preferred range of the volatile topical carrier is between 30% to 60% by weight of the composition. Desirable polar, volatile topical carriers that include ethanol, or ethanol in combination with isododecane or dimethicones, typically, comprise 10% to 60% by weight of the composition, most preferably 30% to 50% by weight of the composition. Desirable non-polar, volatile topical carriers typically comprise 10% to 80% by weight of the composition, most preferably 30% to 60% by weight of the composition.

The anhydrous topical composition can provide the foundation or base compositions for numerous alternative embodiments. Alternative embodiments may include a lotion, a cream, an emulsion, a gel, a suspension, an aerosol, and a powder. Desirable alternative embodiments further include an active agent to provide a desired therapeutic function to the anhydrous topical composition. Desirable active agents may be selected from a group consisting of a sunscreen active agent, an insect repellent, a colorant, a fragrance, a pharmaceutical active agent, and combinations thereof present in a sufficient amount to provide their desired effect. Colorants, fragrances, and other dermatological or pharmaceutical active agents can be present in concentrations according to their respective arts.

One embodiment of the invention provides a sunscreen. This "sunscreen topical composition" is an anhydrous topical composition having at least one sunscreen active agent.

One or more sunscreen active agents, that can be used in the present invention, are capable of attenuating all or part of the harmful effects of ultraviolet ("UV") radiation. In addition, the sunscreen active agents must be non-toxic and non-irritating when applied to the skin. Sunscreen active agents are, typically, categorized into four groups, as follows.

A first group of sunscreen active agents includes ultraviolet A long-wave or "UVA" sunscreen active agents. UVA sunscreen active agents, for example, include a member selected from the group Consisting of avobenzone, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, and combinations thereof.

A second group of sunscreen active agents include ultraviolet B shortwave or "UVB" sunscreen active agents. UVB sunscreen active agents, for example, include a member selected from the group consisting of octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, derivatives thereof, and combinations thereof.

A third group of sunscreen active agents include sunscreen active agents that absorb both UVA and UVB radiation. These full spectrum UV active agents include a member selected from the group consisting of, for example, oxybenzone, meradimate, titanium dioxide, zinc oxide, bis-octrizole, bemotrizinol, drometrizole trisiloxane, sulisobenzone, dioxybenzone, and combinations thereof. Further, surface treated zinc oxides or titanium dioxides including, but not limited to, the proprietary commercial products, Zano 10 Plus and UV-Titan M262, can be used as a full spectrum sunscreen active agent.

The fourth group of sunscreen active agents include encapsulated UV filters. Encapsulated UV filters include a member selected from the group consisting of AvoCap (encapsulated Avobenzone 60% payload and 15% of Octocrylene), OmcCap (encapsulated Octyl Methoxycinnamate, 60% payload), OxyCap (encapsulated Oxybenzone, 47% payload and Octocrylene 20%), HomCap (encapsulated Homosalate, 60% payload), OctiCap, (encapsulated Octisalate 60% payload), ZinoCap (encapsulated ZnO, 70% payload), TitanCap (encapsulated $TiO_2$: 70% payload).

The selection of one or more sunscreen active agents, for use in a sunscreen embodiment of the invention, is made in accordance with the desired objectives for the final product. For example, consumers often desire a full spectrum of UV protection to lessen the risk of cancer and accelerated skin aging from prolonged sun exposure. Some consumers desire a limited exposure of UV radiation to acquire some tanning effects from sun exposure, while minimizing the risk of burning.

Another embodiment of the invention provides an insect repellent. This "insect repellent topical composition" is an anhydrous topical composition having at least one insect repellent.

Desirable insect repellents include, but are not limited to, a member selected from the group consisting of N,N diethyl-m-toluamide (DEET), ethyl butylacetylaminopropionate (IR3535 by Merck Co.), hydroxyethyl isobutyl piperidine carboxylate, oil of citronella, soy bean oil, lemon grass oil, geranium/geraniol oil, neem oil and other natural essential oils, p-menthane-3,8-diol, or any mixtures thereof. Preferred insect repellent active agents may include DEET, ethyl butylacetylaminopropionate, p-menthane-3,8-diol, and oil of citronella. Further, a fragrance is often added to the Insect repellent compositions.

The insect repellent desirably comprises between 1% to 20% by weight of the composition. A preferred range of insect repellent is between 5% to 10% by weight of the composition.

Another embodiment of the invention provides a colorant. This "colorant topical composition" is an anhydrous topical composition having at least one colorant.

Desirable colorants can be an organic or an inorganic pigment or dye. Colorants that can be used in the present compositions include, but are not limited to, proprietary commercial products selected from the group consisting of D&C Red No. 3, D&C Red No. 6, D&C Red No. 7, D&C Red No. 8, D&C Red No. 9, D&C Red No. 21, D&C Red No. 22, DSC Red No. 27, D&C Red No. 28, D&C Red No. 30, D&C Red No. 33, D&C Red No. 34, D&C Red No. 36, FD&C Red No. 40, D&C Yellow No. 5, FD&C Yellow No. 5, FD&C Yellow No. 6, D&C Yellow No. 10, DSC Green No. 3, D&C Green No. 5, D&C Grange No. 5, FD&C Blue No. 1, annatto, copper powder, bismuth oxychloride, guanine, bronze powder, iron oxides, caramel, manganese violet, carmine, mica, titanium dioxide-coated mica, carotene, titanium dioxide, zinc oxide, self-tanning compounds such as dihydroxyacetone (DHA) and erythruloses, and any combinations thereof. Further, the colorant can be an encapsulated pigment or colorant, including, but not limited to, a member selected from the group consisting of TagraCap 1, RedCap 1, Black Cap 1, YellowCap 1, WhiteCap 1, BlueCap 1, MicaCap 1, TagraCap 3, RedCap 3, Black Cap 3, YellowCap 3, BrownCap 3, TagraCap 5, RedCap 5, Black Cap 5, YellowCap 5, BlueCap 5, Red7Cap, CarbonCap, CameleonCaps, and combinations thereof.

The colorant desirably comprises between 0.5% and 10% by weight of the composition. A preferred range of colorant is between 0.5% and 5% by weight of the composition.

Alternative embodiments may comprise other therapeutic or cosmetic active agents such as, but not limited to, amino acids; moisturizers; pH adjusters; perfumes; essential oils; essential fatty adds; sphingolipids; antioxidants; chelating agents; emollients; humectants; moisturizers; minerals; keratolytics; retinoids; hormones; alpha-keto acids; anti-mycobacterial agents; anti-fungal agents; anti-microbials; anti-virals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; skin cooling compounds; skin warming compounds; skin protectants; skin penetration enhancers; exfoliants;

lubricants; depigmenting agents; hypopigmenting agents; pharmaceutical agents; photostabilizing agents; plant extracts; absorbents; salicylic acid; alpha and beta hydroxy acids; vitamins including vitamins A, C, and E; retinal and its derivatives; or any combination of the foregoing. It should be appreciated and understood that this list is not limiting, and that various other active ingredients may be used in the present sunscreen formulations.

Further embodiments of the invention can comprise other topical compositions for human, veterinarian, horticultural, and other coated substrates. Desirable embodiments include combinations of two or more of the already listed embodiments. For example, another embodiment of an anhydrous topical composition comprises an anhydrous topical composition having at least one film former having a surface tension lower than 35 dynes/cm, at least one particle, a volatile topical carrier, a colorant, and a sunscreen active agent, wherein the anhydrous topical composition has an initial water contact angle greater than 60 degrees, preferably greater than 90 degrees, and preferably greater than 100 degrees. Another embodiment of an anhydrous topical composition comprises an anhydrous topical composition having at least one film former having a surface tension lower than 35 dynes/cm, at least one hydrophobic particle, a volatile topical carrier, an insect repellent, and a sunscreen active, where the anhydrous topical composition maintains a water contact angle greater than 60 degrees after 40 minutes.

Preparing the anhydrous topical composition can be performed using a multi-phase approach mixing two or more phases together that are known to one of ordinary skill in the art. A phase can contain a certain set of components that are mixed together before being combined with another phase. The order of mixing the phases is determined by the compositions of the particular phases being mixed in each process step and the desired final product (e.g., a lotion, a cream, an aerosol, etc.)

The following processes illustrate exemplary methods for producing the invention. Variations of these processes and other processes can be used for producing the anhydrous topical composition.

Compounds in a Phase A may be mixed together at room temperature, with or without heat, with propeller mixing to ensure all components are homogenous. Compounds in a Phase B may be mixed together in a separate container, one at a time, until a component is completely dissolved. The Phase B mixture is then homogenized for three minutes at 4000 RPM. Phase B is then added into Phase A. Compounds in a Phase C may be mixed together in another separate container, and subsequently homogenized for four minutes at 4000 RPM. The Phase C mixture is then added to the Phase A and B mixture with mixing.

Alternatively, two or more phases are miscible with one another such that each phase is mixed together or one or more components are dissolved in another component to form a neat solution. This process can produce lotion, a cream, a solution, or a volatile liquid. For example only, compounds in a Phase A may be mixed together at room temperature with a propeller mixing. Compounds in a Phase B may be mixed together in a separate container, one at a time, until all components are completely dissolved. The Phase B mixture is then homogenized then added into Phase A.

Once the two or more phases of the composition are properly mixed together to produce a final composition, depending on individual embodiments, a PMMA plate (i.e., an HD6 plate sold by HelioScreen Labs) is coated with 2 mg/cm² of the inventive composition. This coating thickness is recommended by the United States Food and Drug Administration as an optimal dose for sunscreen application, and this concentration is used herein for consistency.

Figure 1:
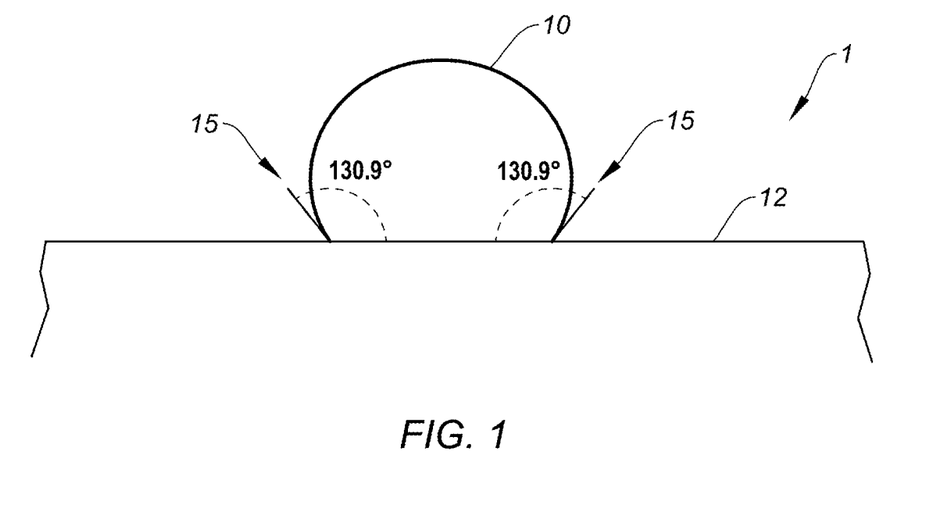
FIG. 1 illustrates a measurement of a water contact angle for Example 9 at 138.2 degrees measured with a Kruss Drop Shape Analysis System DSA 100.
Figure 2:
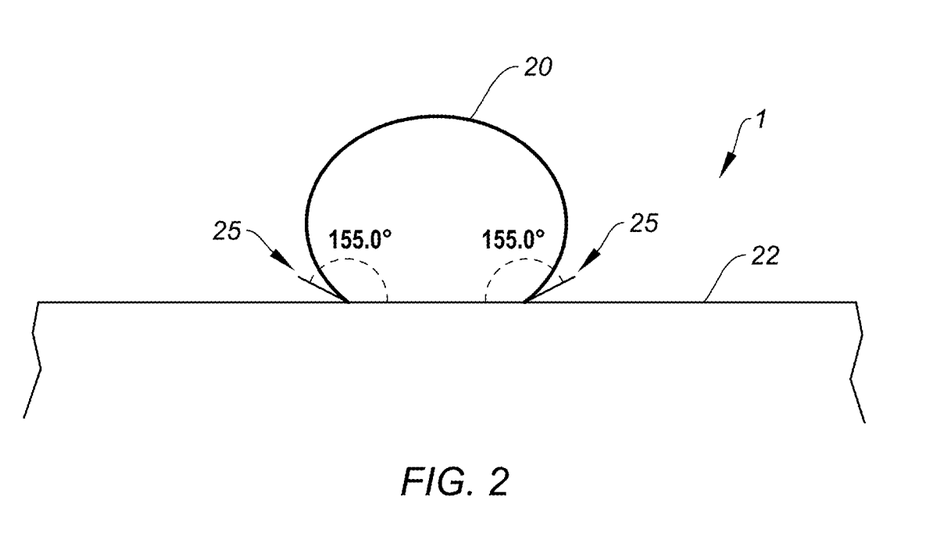
FIG. 2 illustrates another measurement of a water contact angle for Example 18 at 155 degrees measured with a Kruss Drop Shape Analysis System DSA 100.

A contact angle/surface tension or "drop shape" analyzer is used to measure the water contact angle of a composition. FIG. 1 illustrates an initial water contact angle of 130.9 degrees, which was achieved by an embodiment of the present invention, Example 9. A water drop 10 is formed on a composition surface 12 placed on a drop shape analyzer 1. The angle 15 of the water drop 10 measured at the composition surface 12 is the "water contact angle" for the sample of composition being measured. FIG. 2 illustrates a water contact angle of 155.00 degrees, which was achieved by another embodiment of the present invention, Example 18. A water drop 20 is formed on another composition surface 22 placed on a drop shape analyzer 1. The angle 25 of the water drop 20 measured at the composition surface 22 is the "water contact angle" for the sample of composition being measured.

EXAMPLES

The following examples illustrate a representative sampling of the many possible embodiments of the anhydrous topical composition. A brief description of the compounds included in the composition, the process used in preparing the composition, and the resulting water contact angle of the composition are included for each embodiment. These examples are provided in order to demonstrate the many possible anhydrous topical compounds covered by the present invention and not as a limitation on the scope of the present invention. All examples disclosed herein used a Kruss Drop Shape Analysis System DSA 100 to measure the initial and subsequent water contact angles of the anhydrous topical composition and its various embodiments on the specified surfaces. The initial water contact angles of Examples 1 to 23 are shown below. A needle with a diameter of 1.8 mm was used to form the water droplets. Unless otherwise stated, each composition was coated onto a HD6 PMMA plate from Helioscreen Labs at a thickness of 2 mg/cm² and kept at 30° C. for 20 minutes to evaporate any solvent and form a continuous film on the plate. The percentage by weight of each component included in the exemplary composition is shown below in each phase.

Example 1 illustrates an embodiment of the invention that is a sunscreen.

| Phase | Material Name | % by Weight |
|---|---|---|
| PHASE A | Trifluoropropyldimethylsiloxy/Trimethylsiloxy Silsesquioxane (and) Dimethicone (SILFORM FR-5) | 8.00 |
| | Isododecane | 5.00 |
| | Ethanol | 15.00 |
| | Silica dimethyl silylate (HDK H18) | 2.00 |
| | Silica dimethicone silylate (CAB-O-SIL TS-720) | 2.00 |
| PHASE B | Ethanol | 45.20 |
| | Trihydroxystearin (THIXCIN R) | 1.50 |
| PHASE C | Isododecane | 15.00 |
| | Polyhydroxystearic acid (DISPERSUN DSP-OL100) | 0.30 |
| | Titanium Dioxide (And) Alumina (And) Dimethicone (UV-Titan M262) | 3.50 |
| | Zinc Oxide and Triethoxycaprylylsilane (Zano 10 Plus) | 4.00 |
| TOTAL | | 100.00 |

WATER CONTACT ANGLE: 145.7

Example 2 illustrates an embodiment of the invention that is a sunscreen.

| Phase | Material Name | % by Weight |
|---|---|---|
| PHASE A | Trifluoropropyldimethylsiloxy/Trimethylsiloxy Silsesquioxane (and) Dimethicone (SILFORM FR-5) | 8.00 |
| | Cyclic methylsiloxane (Dow Corning D5&D6) | 5.00 |
| | Isododecane | 8.00 |
| | Ethanol | 10.00 |
| | Homosalate | 2.00 |
| | Octisalate | 3.00 |
| | Silica dimethyl silylate (HDK H18) | 1.00 |
| | Silica dimethicone dilylate (CAB-O-SIL ® TS-720) | 3.00 |
| PHASE B | Silica (MSS-500/20N) | 4.00 |
| | Ethanol | 34.20 |
| | Trihydroxystearin (THIXCIN R) | 1.50 |
| PHASE C | Isododecane | 15.00 |
| | Polyhydroxystearic acid (DISPERSUN DSP-OL100) | 0.30 |
| | Zinc Oxide and Triethoxycaprylylsilane (Zano 10 Plus) | 5.00 |
| TOTAL | | 100.00 |

WATER CONTACT NGLE: 106.4

Example 3 illustrates an embodiment of the invention that is a sunscreen.

| Phase | Material Name | % by Weight |
|---|---|---|
| PHASE A | Trifluoropropyldimethylsiloxy/Trimethylsiloxy Silsesquioxane (and) Dimethicone (SILFORM FR-5) | 8.00 |
| | Cyclic methylsiloxane (Dow Corning D5&D6) | 5.00 |
| | Isododecane | 8.00 |
| | Ethanol | 10.00 |
| | Homosalate | 2.00 |
| | Octisalate | 3.00 |
| | Silica dimethyl silylate (HDK H18) | 1.00 |
| | Silica Dimethicone Silylate (CAB-O-SIL TS-720) | 3.00 |
| | Marshmallow Powder (HDI/Trimethylol Hexyl-lactone Crosspolymer (and) Polymethyl Methacrylate) | 4.00 |
| PHASE B | Ethanol | 34.20 |
| | Trihydroxystearin (THIXCIN R) | 1.50 |
| PHASE C | Isododecane | 15.00 |
| | Polyhydroxystearic acid (DISPERSUN DSP-OL100) | 0.30 |
| | Zinc Oxide and Triethoxycaprylylsilane (Zano 10 Plus) | 5.00 |
| TOTAL | | 100.00 |

WATER CONTACT ANGLE: 103.0 degrees

Example 4 illustrates an embodiment of the invention that is a sunscreen.

| Phase | Material Name | % by Weight |
|---|---|---|
| PHASE A | Trifluoropropyldimethylsiloxy/Trimethylsiloxy Silsesquioxane (and) Dimethicone (SILFORM FR-5) | 8.00 |
| | Cyclopentasiloxane/Cyclohexasiloxane (Dow Corning D5&D6) | 5.00 |
| | Isododecane | 8.00 |
| | Ethanol | 10.00 |
| | Homosalate | 2.00 |
| | Octisalate | 3.00 |
| | Silica dimethyl silylate (HDK H18) | 1.00 |
| | Silica silylate (CAB-O-SIL TS-610) | 3.00 |
| | Cellulose (CELLULOBEADS) D-50 | 4.00 |
| PHASE B | Ethanol | 34.20 |
| | Trihydroxystearin (THIXCIN R) | 1.50 |
| PHASE C | Isododecane | 15.00 |
| | Polyhydroxystearic acid (DISPERSUN DSP-OL100) | 0.30 |
| | Zinc Oxide and Triethoxycaprylylsilane (Zano 10 Plus) | 5.00 |
| TOTAL | | 100.00 |

WATER CONTACT ANGLE: 107.1

Example 5 illustrates an embodiment of the invention that is a sunscreen.

| Phase | Material Name | % by Weight |
|---|---|---|
| PHASE A | Trifluoropropyldimethylsyloxy/Trimethylsiloxy Silsesquioxane (and) Dimethicone (SILFORM FR-5) | 8.00 |
| | Isododecane | 8.00 |
| | Ethanol | 15.00 |
| | Silica dimethyl silylate (HDK H18) | 1.00 |
| | Silica dimethicone silylate (CAB-O-SIL TS-720) | 3.00 |
| | Silica (MSS-500/20N) | 4.00 |
| PHASE B | Ethanol | 36.70 |
| | Trihydroxystearin (THIXCIN R) | 1.50 |
| PHASE C | Isododecane | 15.00 |
| | Polyhydroxystearic acid (Dispersun DSP-OL100) | 0.30 |
| | Titanium Dioxide (And) Alumina (And) Dimethicone (UV-Titan M262) | 3.50 |
| | Zinc oxide and Triethoxycaprylylsilane (Zano 10 Plus) | 4.00 |
| TOTAL | | 100.00 |

WATER CONTACT ANGLE: 130.6

Example 6 illustrates an embodiment of the invention that is a sunscreen.

| Phase | Material Name | % by Weight |
|---|---|---|
| PHASE A | Trifluoropropyldimethylsyloxy/Trimethylsiloxy Silsesquioxane (and) Dimethicone (SILFORM FR-5) | 8.00 |
| | Perfluorononyl Dimethicone (PECOSIL FSH-300) | 3.00 |
| | Isododecane | 8.00 |
| | Ethanol | 15.00 |
| | Homosalate | 2.00 |
| | Octisalate | 3.00 |
| | Silica dimethyl silylate (HDK H18) | 1.00 |
| | Silica dimethicone silylate (CAB-O-SIL TS-720) | 3.00 |
| | Silica (MSS-500/20N) | 4.00 |
| PHASE B | Ethanol | 30.70 |
| | Trihydroxystearin (THIXCIN R) | 2.00 |
| PHASE C | Isododecane | 15.00 |
| | Polyhydroxystearic acid (DISPERSUN DSP-OL100) | 0.30 |
| | Zinc Oxide and Triethoxycaprylylsilane (ZANO 10 Plus) | 5.00 |
| TOTAL | | 100.00 |

WATER CONTACT ANGLE: 104.1

Example 7 illustrates an embodiment of the invention that is a sunscreen.

| Phase | Material Name | % by Weight |
|---|---|---|
| PHASE A | Trifluoropropyldimethylsiloxy/ Trimethylsiloxy Silsesquioxane (and) Dimethicone (SILFORM FR-5) | 8.00 |
| | Cyclopentasiloxane and dimethicone/vinyl dimethicone crosspolymer and perfluorononyl dimethicone (SILMER G162F) | 5.00 |
| | Isododecane | 8.00 |
| | Ethanol | 15.00 |
| | Homosalate | 2.00 |
| | Octisalate | 3.00 |
| | Silica dimethyl silylate (HDK H18) | 1.00 |
| | Silica dimethicone silylate (CAB-O-SIL TS-720) | 3.00 |
| | Silica (MSS-500/20N) | 4.00 |
| PHASE B | Ethanol | 28.70 |
| | Trihydroxystearin (THIXCIN R) | 2.00 |
| PHASE C | Isododecane | 15.00 |
| | Polyhydroxystearic acid (DISPERSUN DSP-OL100) | 0.30 |
| | Zinc Oxide and Triethoxycaprylylsilane (Zano 10 Plus) | 5.00 |
| TOTAL | | 100.00 |

WATER CONTACT ANGLE: 102.7

Example 8 illustrates an embodiment of the invention that is a sunscreen.

| Phase | Material (INCI Name) | % by Weight |
|---|---|---|
| PHASE A | Trifluoropropyldimethylsiloxy/ Trimethylsiloxy Silsesquioxane (and) Dimethicone (SILFORM FR-5) | 8.00 |
| | Isododecane | 8.00 |
| | Ethanol | 15.00 |
| | Homosalate | 2.00 |
| | Octisalate | 3.00 |
| | $C_{30-45}$ Alkyldimethylsilyl Polypropylsilsesquioxane (Dow Corning SW-8005 $C_{30}$ Resin Wax) | 2.00 |
| | Silica dimethyl silylate (HDK H18) | 1.00 |
| | Silica dimethicone silylate (CAB-O-SIL TS-720) | 3.00 |
| PHASE B | Ethanol | 35.70 |
| | Trihydroxystearin (THIXCIN R) | 2.00 |
| PHASE C | Isododecane | 15.00 |
| | Polyhydroxystearic acid (DISPERSUN DSP-OL100) | 0.30 |
| | Zinc Oxide and Triethoxycaprylylsilane (Zano 10 Plus) | 5.00 |
| TOTAL | | 100.00 |

WATER CONTACT ANGLE: 101.8

Example 9 illustrates an embodiment of the invention that is a sunscreen with a colorant.

| Phase | Material (INCI Name) | % by Weight |
|---|---|---|
| PHASE A | Trifluoropropyldimethylsiloxy/ Trimethylsiloxy Silsesquioxane (and) Dimethicone (SILFORM FR-5) | 8.00 |
| | Isododecane | 8.00 |
| | Ethanol | 15.00 |
| | Silica dimethyl silylate (HDK H18) | 1.00 |
| | Silica dimethicone silylate (CAB-O-SIL TS-720) | 3.00 |
| | Silica (MSS-500/20N) | 4.00 |
| | Synthetic fluorphlogopite (and) titanium dioxide (and) iron oxides (and) tin oxide (SYNCRYSTAL ® Ivory Pigment) | 1.00 |
| PHASE B | Ethanol | 35.20 |
| | Trihydroxystearin (THIXCIN R) | 2.00 |
| PHASE C | Isododecane | 15.00 |
| | Polyhydroxystearic acid (DISPERSUN DSP-OL100) | 0.30 |
| | Titanium Dioxide (And) Alumina (And) Dimethicone (UV-Titan M262) | 3.50 |
| | Zinc Oxide and Triethoxycaprylylsilane (Zano 10 Plus) | 4.00 |
| TOTAL | | 100.00 |

WATER CONTACT ANGLE: 138.2

Example 10 illustrates an embodiment of the invention that is a sunscreen composition.

| Phase | Material (INCI Name) | % by Weight |
|---|---|---|
| PHASE A | Alcohol (and) Crotonic Acid/Vinyl $C_{8-12}$ Isoalkyl Esters/VA/Bis-Vinyldimethicone | 8.00 |
| | Ethanol | 15.00 |
| | Homosalate | 5.00 |
| | Silica Dimethicone Silylate (CAB-O-SIL TS-720) | 4.00 |
| PHASE B | Ethanol | 68.00 |
| TOTAL | | 100.00 |

WATER CONTACT ANGLE: 102.6

Example 11 illustrates an embodiment of the invention that is a sunscreen composition.

| Phase | Material (INCI Name) | % by Weight |
|---|---|---|
| PHASE A | Alcohol (and) Crotonic Acid/Vinyl $C_{8-12}$ Isoalkyl Esters/VA/Bis-Vinyldimethicone | 8.00 |
| | Ethanol | 15.00 |
| | Homosalate | 5.00 |
| | Silica Dimethicone Silylate (CAB-O-SIL TS-720) | 4.00 |
| PHASE B | Ethanol | 68.00 |
| TOTAL | | 100.00 |

WATER CONTACT ANGLE: 109.7

Example 12 illustrates an embodiment of the invention that is a sunscreen composition.

| Phase | Material (INCI Name) | % by Weight |
|---|---|---|
| PHASE A | Alcohol (and) Crotonic Acid/Vinyl $C_{8-12}$ Isoalkyl Esters/VA/Bis-Vinyldimethicone Crosspolymer (BELSIL P1101) | 8.00 |
| | Ethanol | 15.00 |
| | Octylcrylene | 5.00 |
| | Silica dimethicone silylate (CAB-O-SIL TS-720) | 4.00 |
| PHASE B | Ethanol | 68.00 |
| TOTAL | | 100.00 |

WATER CONTACT ANGLE: 110.0

Example 13 illustrates an embodiment of the invention that is a sunscreen.

| Phase | Material Name | % by Weight |
|---|---|---|
| PHASE A | Alcohol (and) Crotonic Acid/Vinyl C$_{8-12}$ Isoalkyl Esters/VA/Bis-Vinyldimethicone Crosspolymer (BELSIL P1101) | 8.00 |
|  | Ethanol | 15.00 |
|  | Silica dimethicone silylate (CAB-O-SIL TS-720) | 4.00 |
| PHASE B | Ethanol | 66.00 |
|  | Trihydroxystearin (THIXCIN R) | 2.00 |
| PHASE C | Zinc Oxide and Triethoxycaprylylsilane (Zano 10 Plus) | 5.00 |
| TOTAL |  | 100.00 |

WATER CONTACT ANGLE: 136.2

Example 14 illustrates an embodiment of the invention that is a sunscreen.

| Phase | Material Name | % by Weight |
|---|---|---|
| PHASE A | Alcohol (and) Crotonic Acid/Vinyl C$_{8-12}$ Isoalkyl Esters/VA/Bis-Vinyldimethicone | 8.00 |
|  | Ethanol | 15.00 |
|  | Avobenzone | 3.00 |
|  | Silica dimethicone silylate | 4.00 |
| PHASE B | Ethanol | 68.00 |
|  | Trihydroxystearin (THIXCIN R) | 2.00 |
| TOTAL |  | 100.00 |

WATER CONTACT ANGLE: 142.1

Example 15 illustrates an embodiment of the invention that is a sunscreen.

| Phase | Material Name | % by Weight |
|---|---|---|
| PHASE A | Alcohol (and) Crotonic Acid/Vinyl C$_{8-12}$ Isoalkyl Esters/VA/Bis-Vinyldimethicone Crosspolymer (BELSIL P1101) | 8.00 |
|  | Ethanol | 15.00 |
|  | Oxybenzone | 6.00 |
|  | Silica dimethicone silylate (CAB-O-SIL TS-720) | 4.00 |
| PHASE B | Ethanol | 65.00 |
|  | Trihydroxystearin (THIXCIN R) | 2.00 |
| TOTAL |  | 100.00 |

WATER CONTACT ANGLE: 117.3

Example 16 illustrates an embodiment of the invention that is a sunscreen.

| Phase | Material Name | % by Weight |
|---|---|---|
| PHASE A | Alcohol (and) Crotonic Acid/Vinyl C$_{8-12}$ Isoalkyl Esters/VA/Bis-Vinyldimethicone Crosspolymer (BELSIL P1101) | 8.00 |
|  | Ethanol | 15.00 |
|  | Avobenzone | 3.00 |
|  | Oxybenzone | 6.00 |
|  | Silica dimethicone silylate (CAB-O-SIL TS-720) | 4.00 |
| PHASE B | Ethanol | 62.00 |
|  | Trihydroxystearin (THIXCIN R) | 2.00 |
| TOTAL |  | 100.00 |

WATER CONTACT ANGLE: 124.2

Example 17 illustrates an embodiment of the invention that is a topical composition.

| Phase | Material (INCI Name) | % by Weight |
|---|---|---|
| PHASE A | Alcohol (and) Crotonic Acid/Vinyl C$_{8-12}$ Isoalkyl Esters/VA/Bis-Vinyldimethicone | 8.00 |
|  | Ethanol | 67.7 |
|  | Silica Dimethicone Silylate (CAB-O-SIL TS-720) | 4.00 |
|  | Synthetic fluorphlogopite (and) titanium dioxide (and) iron oxides (and) tin oxide (SYNCRYSTAL Ivory Pigment) | 1.00 |
| Phase B | Isododecane | 15.00 |
|  | Polyhydroxystearic acid (DISPERSUN DSP-OL100) | 0.30 |
|  | Zinc Oxide and Triethoxycaprylylsilane (Zano 10 Plus) | 5.00 |
| TOTAL |  | 100.00 |

WATER CONTACT ANGLE: 126.8

Example 18 illustrates an embodiment of the invention that is a topical delivery system.

| Phase | Material (INCI Name) | % by Weight |
|---|---|---|
| PHASE A | Alcohol (and) Crotonic Acid/Vinyl C$_{8-12}$ Isoalkyl Esters/VA/Bis-Vinyldimethicone | 8.00 |
|  | Ethanol | 15.00 |
|  | Silica dimethicone silylate (CAB-O-SIL TS-720) | 4.00 |
| PHASE B | Ethanol | 71.00 |
|  | Trihydroxystearin (THIXCIN R) | 2.00 |
| TOTAL |  | 100.00 |

WATER CONTACT ANGLE: 155.0

Example 19 illustrates an embodiment of the invention that is a topical delivery system.

| Phase | Material Name | % by Weight |
|---|---|---|
| PHASE A | Alcohol (and) Crotonic Acid/Vinyl C$_{8-12}$ Isoalkyl Esters/VA/Bis-Vinyldimethicone | 8.00 |
|  | Perfluorononyl Dimethicone (PECOSIL FSH-300) | 3.00 |
|  | Ethanol | 15.00 |
|  | Silica dimethicone silylate (CAB-O-SIL TS-720) | 4.00 |
|  | Polymethylsilsesquioxane (And) Perfluorooctyl Triethoxysilane (MST-547-FS) | 2.00 |
| PHASE B | Ethanol | 68.00 |
| TOTAL |  | 100.00 |

WATER CONTACT ANGLE: 137.5

Example 20 illustrates an embodiment of the invention that is a topical delivery system.

| Phase | Material Name | % by Weight |
|---|---|---|
| PHASE A | Alcohol (and) Crotonic Acid/Vinyl $C_{8-12}$ Isoalkyl Esters/VA/Bis-Vinyldimethicone | 8.00 |
|  | Ethanol | 15.00 |
|  | Silica dimethicone silylate (CAB-O-SIL TS-720) | 4.00 |
| PHASE B | Ethanol | 73.00 |
| TOTAL |  | 100.00 |

WATER CONTACT ANGLE: 155.9

Example 21 illustrates an embodiment of the invention that is a topical delivery system.

| Phase | Material Name | % by Weight |
|---|---|---|
| PHASE A | Alcohol (and) Crotonic Acid/vinyl $C_{8-12}$ Isoalkyl Esters/VA/Bis-Vinyldimethicone | 8.00 |
|  | Perfluorononyl Dimethicone (PECOSIL FSH-300) | 3.00 |
|  | Ethanol | 15.00 |
|  | Silica dimethicone silylate (CAB-O-SIL TS-720) | 4.00 |
| PHASE B | Ethanol | 68.00 |
|  | Trihydroxystearin (THIXCIN R) | 2.00 |
| TOTAL |  | 100.00 |

WATER CONTACT ANGLE: 130.5

Example 22 illustrates an embodiment of the invention that is a sunscreen.

| Phase | Material Name | % by Weight |
|---|---|---|
| PHASE A | Avobenzone | 3.00 |
|  | Octocrylene | 3.00 |
|  | Homosalate | 5.50 |
|  | Octisalate | 4.50 |
|  | Phenethyl Benzoate | 8.00 |
|  | Propylparaben | 0.18 |
|  | $C_{30-45}$ Alkyl Methicone (and) $C_{30-45}$ Olefin | 2.00 |
| PHASE B | Trifluoropropyldimethylsiloxy/Trimethylsiloxy Silsesquioxane (and) Dimethicone | 8.00 |
|  | Perfluorononyl Dimethicone | 3.00 |
|  | Isododecane | 30.00 |
|  | Disiloxane | 17.82 |
|  | Tryhydroxystearin | 2.50 |
|  | $C_{12-15}$ Alkyl Benzoate (and) Stearalkonium Hectorite (and) Propylene Carbonate | 1.50 |
|  | Silica Dimethicone Silylate | 6.00 |
|  | Polymethylsilsesquioxane (and) Perfluorooctyl Triethoxysilane | 2.00 |
|  | Caprylyl Methicone (and) PEG-12 Dimethicone/PPG-20 Crosspolymer | 2.70 |
| PHASE C | Fragrance | 0.30 |
| TOTAL |  | 100.00 |

WATER CONTACT ANGLE: 95.9

Example 23 illustrates an embodiment of the invention that is a sunscreen.

| Phase | Material Name | % by Weight |
|---|---|---|
| PHASE A | Oxybenzone | 3.00 |
|  | Octocrylene | 2.00 |
|  | Homosalate | 2.00 |

-continued

| Phase | Material Name | % by Weight |
|---|---|---|
|  | Octisalate | 2.00 |
|  | Diisopropyl Adipate | 2.00 |
|  | Ethylhexyl Methoxycrylene | 3.00 |
|  | $C_{30-45}$ Alkyl Methicone and $C_{30-45}$ Olefin | 2.00 |
|  | Propylparaben | 0.18 |
| PHASE B | Trimethylsiloxysilicate | 2.00 |
|  | Perfluorononyl Dimethicone | 3.00 |
|  | Isododecane | 15.00 |
|  | Disiloxane | 24.95 |
|  | Trihydroxystearin | 4.00 |
|  | $C_{12-15}$ Alkyl Benzoate (and) Stearalkonium Hectorite (and) Propylene Carbonate | 1.500 |
|  | Silica Dimethicone Silylate | 4.00 |
|  | Isododecane (and) Dimethicone/Bis-Isobutyl PPG-20 Crosspolymer | 6.67 |
| PHASE C | Isododecane | 15.00 |
|  | Polyhydroxystearic acid | 0.400 |
|  | Zinc Oxide (and) Triethoxycaprylylsilane | 7.00 |
| PHASE D | Fragrance | 0.30 |
| TOTAL |  | 100.00 |

WATER CONTACT ANGLE: 104.9

Figure 3:
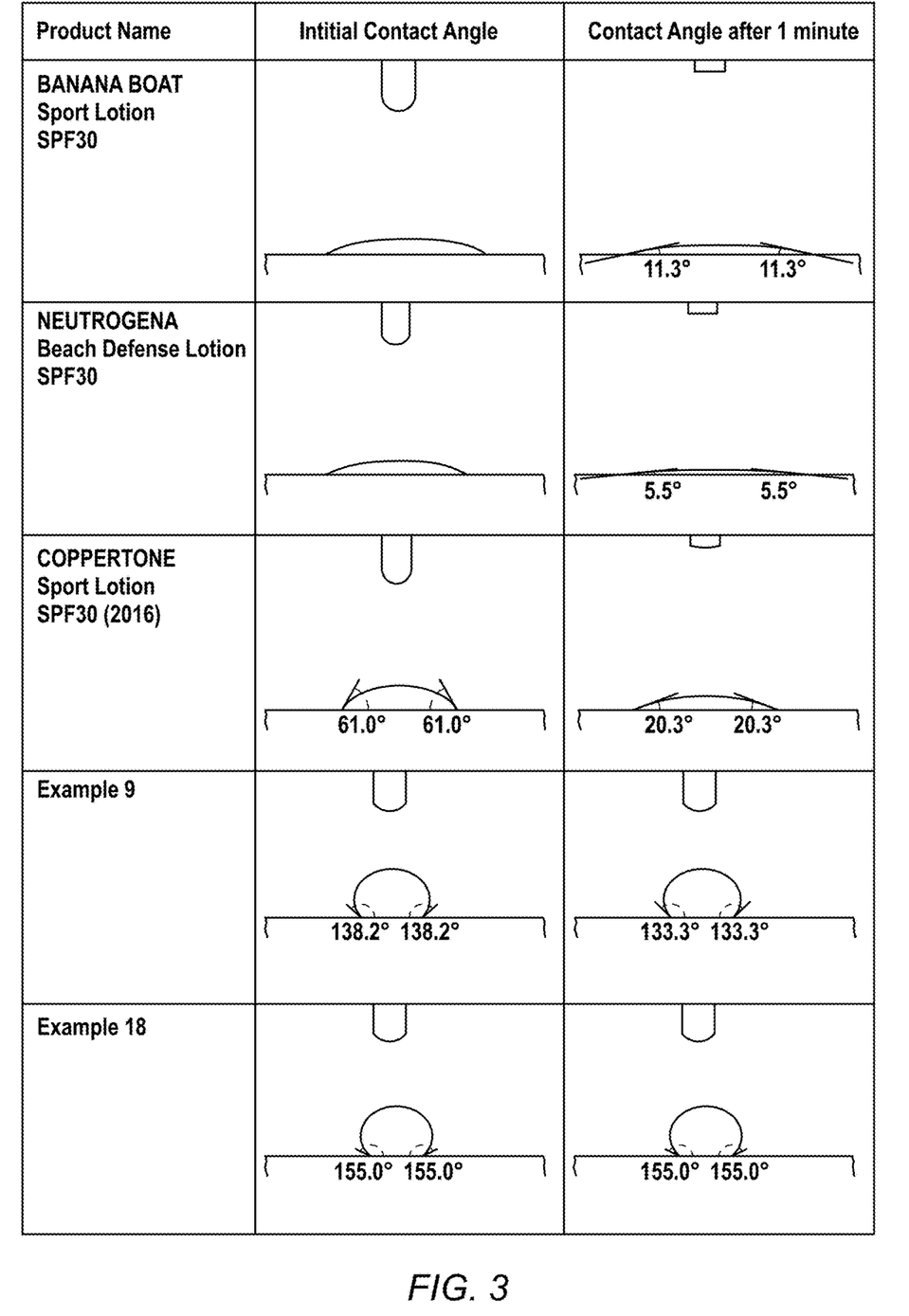
FIG. 3 are photographic images of the initial water contact angles of commercially available sunscreens and inventive compositions, and the water contact angles after one (1) minute.

Representative of the unexpected results of the inventive compositions, are the initial water contact angles of the inventive compositions Examples 9 and 18, and after one (1) minute, in comparison with commercially available sunscreen compositions are presented shown in FIG. 3 and tallied in Table 3 below.

TABLE 3

| Name | Initial Contact Angle | Contact Angle after 1 minute |
|---|---|---|
| BANANA BOAT Sport Lotion SPF30 | 30.0 | 11.3 |
| NEUTROGENA Beach Defense Lotion SPF30 | 20.0 | 5.5 |
| COPPERTONE Sport Lotion SPF30 (2016) | 60.1 | 20.3 |
| Example 9 | 138.2 | 133.3 |
| Example 18 | 155.0 | 155.0 |

It was observed that the commercial sunscreen lotion products all had relatively low contact angles to start, and, after one (1) minute, the contact angles quickly decreased due to the water re-emulsification process of these oil-in-water emulsion products. Contrast this with the inventive compositions of Examples 9 and 18 wherein the contact angles did not significantly decrease thereby exhibiting a continuing water repellent effect.

Figure 4:
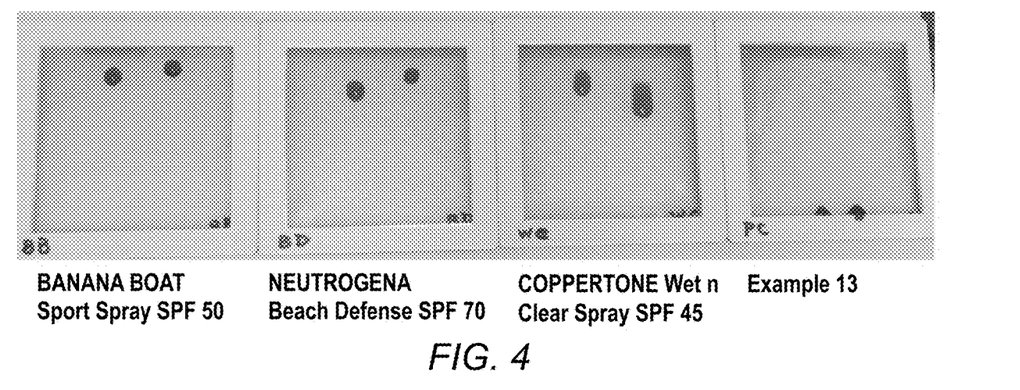
FIG. 4 are photographic images of sunscreen coated Vitro-Skin® after blue water droplets are dripped onto the surface after one (1) second.
Figure 5:
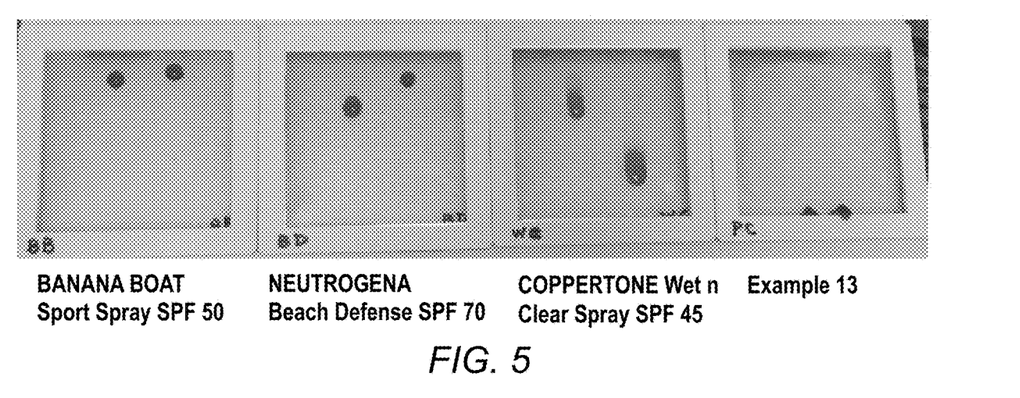
FIG. 5 are photographic images of sunscreen coated Vitro-Skin® after blue water droplets are dripped onto the surface after one (1) minute.

FIG. 4 shows photographic images of VITRO-SKIN coated with commercially available sunscreen compositions and the inventive composition of Example 13 applied at a thickness of 2 mg/cm². The VITRO-SKIN was tilted at a thirty-degree angle (30°). Droplets of water, dyed blue to better show distinction, was dropped onto the top of the VITRO-SKIN plates and the image taken after one (1) second. On the inventive composition, the water droplet quickly rolls to the bottom of the surface without remaining on the VITRO-SKIN sample (as it does with the BANANA BOAT Sport Spray SPF 50 and NEUTROGENA Beach Defense Spray SPF 70) or trailing a tail (as seen in the COPPERTONE Wet N Clear Spray SPF 45). In FIG. 5, the photographic images show the path of water droplets one (1) minute after application on the treated VITRO-SKIN of FIG. 4. Except for the inventive composition, the water droplets remain on the surface.

Figure 6:
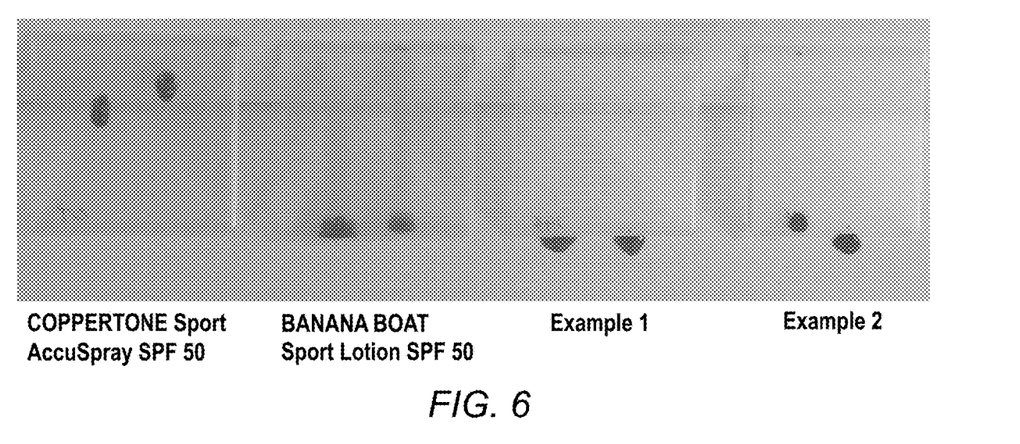
FIG. 6 are photographic images of sunscreen coated PMMA plates after blue water droplets are dripped onto the surface.

FIG. 6 are photographic images showing the same unexpected effects of the inventive compositions of Examples 1 and 2 when the water droplets are applied onto PMMA plates, coated with the sunscreen compositions, as specified, and tilted at 30 degrees. Water droplets applied onto the PMMA plates coated with the inventive compositions of Examples 1 and 2 readily bead up and roll off the plate. The initial contact angles of Examples 1 and 2 are greater than 90 degrees, namely 145.7 degrees and 106.4 degrees, respectively whereas the initial contact angle of the BANANA BOAT Sport Lotion SPF 50 is 17.5 degrees, and the initial contact angle for the COPPERTONE Sport AccuSpray SPF 50 is 69.0 degrees.

Figure 7:
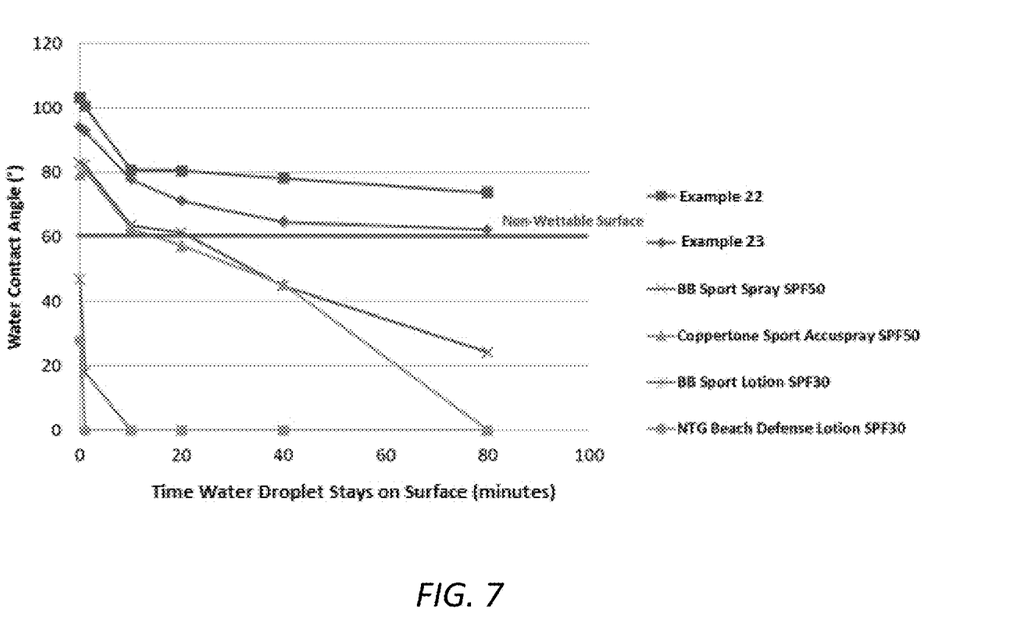
FIG. 7 is a graph comparing the water contact angles of inventive compositions and commercially available sunscreens over a time period of initial contact up to eighty (80) minutes.

FIG. 7 shows a graphic representation of the water contact angles over time from time 0 at the onset of application of the water droplets to at least 80 minutes, which is the time limit for determining water resistance in accordance with the 2011 U.S. Food & Drug Administration (FDA) Final Monograph for Water Resistance. The water contact angles greater than 60 degrees created on the treated surfaces, are considered non-wettable surfaces; the water droplets do not tail or wet the treated surface. Unexpectedly, over time, the water contact angles of the exemplary compositions, Examples 22 and 23 are maintained such that the water repellency is not significantly diminished. Contrast this to the commercially available sunscreen compositions, BANANA BOAT Sport Lotion SPF 50, COPPERTONE Sport AccuSpray SPF 50, and NEUTROGENA Beach Defense Lotion SPF 30, where the contact angles decrease significantly over a very short period of time. in 20 minutes or less, the initial water contact angles have fallen below 60 degrees wetting the surface of the plate.

The compositions of the present invention provide a water repellent finish when topically applied to a keratinous surface such as mammalian skin as determined by a water contact angle greater than 60 degrees, preferably greater than 90 degrees, and most preferably greater than 100 degrees. This water repellency effect has been shown to be maintained over a period of at least 80 minutes.

While the present disclosure has been particularly described, in conjunction with specific preferred embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present disclosure.

The invention claimed is:

1. An anhydrous topical composition comprising:
a water repellant component comprising:
at least one film former comprising a silicone having a surface tension lower than 35 dynes/cm, wherein said silicone comprises $C_{24-28}$ alkyldimethylsiloxy trimethylsiloxysilicate, trifluoropropyldimethylsiloxy/trimethylsiloxy silsesquioxane, or combinations thereof, and wherein said at least one film former is present in an amount of 0.5% to 10% by weight based on a total weight of said anhydrous topical composition;
hydrophobic particles comprising polymethylsilsesquioxane and silica silylate, wherein said polymethylsilsesquioxane is present in an amount greater than 0.5% based on the total weight of said anhydrous topical composition, and wherein said particles are present in an amount up to 10% by weight based on the total weight of said anhydrous topical composition; and
a volatile topical carrier present in an amount of 10% to 80% by weight based on the total weight of said anhydrous topical composition; and
a sunscreen active agent selected from the group consisting of an organic sunscreen active agent, wherein said anhydrous topical composition is free of colorants.

2. The anhydrous topical composition of claim 1, wherein said organic sunscreen active agent is selected from the group consisting of an organic ultraviolet A long-wave sunscreen active agent, an organic ultraviolet B shortwave sunscreen active agent, an organic full spectrum sunscreen active agent, an encapsulated organic ultraviolet filter, or combinations thereof.

3. The anhydrous topical composition of claim 1, further comprising a therapeutic amount of at least one insect repellent selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, natural essential oils, p-menthane-3,8- diol, or combinations thereof.

4. The anhydrous topical composition of claim 1, wherein said anhydrous topical composition has an initial water contact angle greater than 90 degrees.

5. The anhydrous topical composition of claim 1, wherein:
said organic sunscreen active agent comprises avobenzone and further comprises terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimate, bis-octrizole, bemotrizinol, drometrizole trisiloxane, sulisobenzone, dioxybenzone, or combinations thereof; and
said film former further comprises a wax, an ester, a resin, a rosin, or combinations thereof.

6. The anhydrous topical composition of claim 1, further including amino acids moisturizers pH adjusters perfumes essential oils essential fatty acids sphingolipids antioxidants chelating agents emollients humectants moisturizers minerals keratolytics retinoids hormones alpha-keto acids antimycobacterial agents anti-fungal agents anti-microbials anti-virals analgesics anti-allergenic agents H1 or H2 antihistamines anti-inflammatory agents anti-irritants anti-neoplastics immune system boosting agents immune system suppressing agents anti-acne agents anesthetics antiseptics skin cooling compounds skin warming compounds skin protectants skin penetration enhancers exfoliants lubricants depigmenting agents hypopigmenting agents pharmaceutical agents photostabilizing agents plant extracts absorbents salicylic acid alpha and beta hydroxy acids vitamins including vitamins A, C, and E retinol and its derivatives or combinations thereof.

7. The anhydrous topical composition of claim 6, wherein said organic sunscreen active agent comprises avobenzone, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimatebis-octrizole, bemotrizinol, drometrizole trisiloxane, sulisobenzone, dioxybenzone, or combinations thereof.

8. The anhydrous topical composition of claim 6, further comprising at least one insect repellent selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, natural essential oils, p-menthane-3,8-diol, or combinations thereof.

9. The anhydrous topical composition of claim 1, wherein said composition has an initial water contact angle greater than 100 degrees or 150 degrees.

10. The anhydrous topical composition of claim 1, wherein said composition has a water contact angle greater than 60 degrees after 40 minutes or after 80 minutes.

11. The anhydrous topical composition of claim 1, wherein said volatile topical carrier is present in an amount of 30% to 60% by weight based on a total weight of said anhydrous topical composition.

12. The anhydrous topical composition of claim 1, wherein said silicone comprises isododecane (and) $C_{24\text{-}28}$ alkyldimethylsiloxy trimethylsiloxysilicate, cyclopentasiloxane (and) $C_{24\text{-}28}$ alkyldimethylsiloxy trimethylsiloxysilicate, trifluoropropyldimethylsiloxy/trimethylsiloxy silsesquioxane (and) dimethicone, or combinations thereof.

13. The anhydrous topical composition of claim 12, wherein said polymethylsilsesquioxane comprises polymethylsilsesquioxane (and) perfluorooctyl triethoxysilane.

14. The anhydrous topical composition of claim 13, wherein said silica silylate comprises silica dimethicone silylate, silica dimethyl silylate, or combinations thereof.

15. The anhydrous topical composition of claim 1, wherein said volatile topical carrier is non-polar or polar.

16. The anhydrous topical composition of claim 1, wherein said volatile topical carrier comprises ethanol, isododecane, volatile hydrocarbons, volatile silicones, or combinations thereof.

17. The anhydrous topical composition of claim 1, wherein said anhydrous topical composition is in a lotion, a cream, an emulsion, a gel, a suspension, an aerosol, or a powder.

18. The anhydrous topical composition of claim 1, wherein said particles further comprise polytetrafluoroethylene.

19. A topical composition comprising:
a sunscreen active agent selected from the group consisting of an organic sunscreen active agent; and
an anhydrous water repellant component comprising:
at least one film former comprising a silicone having a surface tension lower than 35 dynes/cm, wherein said silicone comprises $C_{24\text{-}28}$ alkyldimethylsiloxy trimethylsiloxysilicate, trifluoropropyldimethylsiloxy/trimethylsiloxy silsesquioxane, or combinations thereof, and wherein said at least one film former is present in an amount of 0.5% to 10% by weight based on a total weight of said topical composition;
hydrophobic particles comprising polymethylsilsesquioxane and silica silylate, wherein said polymethylsilsesquioxane is present in an amount greater than 0.5% based on the total weight of said topical composition, and wherein said particles are present in an amount up to 10% by weight based on the total weight of said topical composition; and
a volatile topical carrier present in an amount of 10% to 80% by weight based on the total weight of said topical composition,
wherein said topical composition is in the form of an emulsion, and wherein said topical composition is free of colorants.

20. The topical composition of claim 19, wherein said organic sunscreen active agent is selected from the group consisting of an organic ultraviolet A long-wave sunscreen active agent, an organic ultraviolet B shortwave sunscreen active agent, an organic full spectrum sunscreen active agent, an encapsulated organic ultraviolet filter, or combinations thereof.

21. The topical composition of claim 19, wherein said polymethylsilsesquioxane is present in an amount greater than 1.0% by weight based on the total weight of said topical composition, and wherein said hydrophobic particles are present in an amount of 5% to 10% by weight based on the total weight of said topical composition.

22. The topical composition of claim 1, wherein said polymethylsilsesquioxane is present in an amount greater than 1.0% by weight based on the total weight of said anhydrous topical composition, and wherein said hydrophobic particles are present in an amount of 5% to 10% by weight based on the total weight of said anhydrous topical composition.

* * * * *